(12) United States Patent
Pattke

(10) Patent No.: US 11,439,526 B2
(45) Date of Patent: Sep. 13, 2022

(54) HAND ORTHOSIS

(71) Applicants:Jörg Pattke, Berlin (DE); Wolfgang Lenze, Enger (DE); Nea International B.V., Maastricht-Airport (NL)

(72) Inventor: Jörg Pattke, Berlin (DE)

(73) Assignees: Jorg Pattke, Berlin (DE); Wolfgang Lenze, Enger (DE); Nea International B.V., Maastricht-Airport (NL)

( * ) Notice: Subject to any disclaimer, the term of this patent is extended or adjusted under 35 U.S.C. 154(b) by 327 days.

(21) Appl. No.: 16/312,228

(22) PCT Filed: Jun. 23, 2017

(86) PCT No.: PCT/DE2017/100533
§ 371 (c)(1),
(2) Date: Dec. 20, 2018

(87) PCT Pub. No.: WO2017/220084
PCT Pub. Date: Dec. 28, 2017

(65) Prior Publication Data
US 2019/0159921 A1    May 30, 2019

(30) Foreign Application Priority Data

Jun. 24, 2016  (DE) .................. 10 2016 111 644.0
Aug. 29, 2016  (DE) .................. 10 2016 116 014.8
Apr. 18, 2017  (EP) ......................... 17 166 900

(51) Int. Cl.
*A61F 5/01* (2006.01)
*A61F 5/10* (2006.01)

(52) U.S. Cl.
CPC .............. *A61F 5/0118* (2013.01); *A61F 5/10* (2013.01); *A61F 2005/0179* (2013.01)

(58) Field of Classification Search
CPC ................ A61F 5/0585; A61F 5/05858; A61F 5/058566; A61F 5/058575;
(Continued)

(56) References Cited

U.S. PATENT DOCUMENTS 1,082,794 A * 12/1913 Boreham .................. F16F 1/26
                                                                                267/53
8,348,810 B2 * 1/2013 Land .................. A63B 21/4025
                                                                                602/5

(Continued)

FOREIGN PATENT DOCUMENTS

DE         43 28 116 C1     1/1995
WO    WO-2016174087 A1 *  11/2016   ......... A41D 19/0024

OTHER PUBLICATIONS

International Search Report and Written Opinion for International Application No. PCT/DE2017/100533, dated Sep. 6, 2017.
(Continued)

*Primary Examiner* — Alireza Nia
*Assistant Examiner* — Gina McCarthy
(74) *Attorney, Agent, or Firm* — Wolf, Greenfield & Sacks, P.C.

(57) ABSTRACT

The invention relates to a hand orthosis comprising a glove and at least one finger splint, wherein the finger splint can be fixed to a hand by means of the glove and wherein the finger splint comprises at least one spring.

14 Claims, 6 Drawing Sheets

Figure 2:
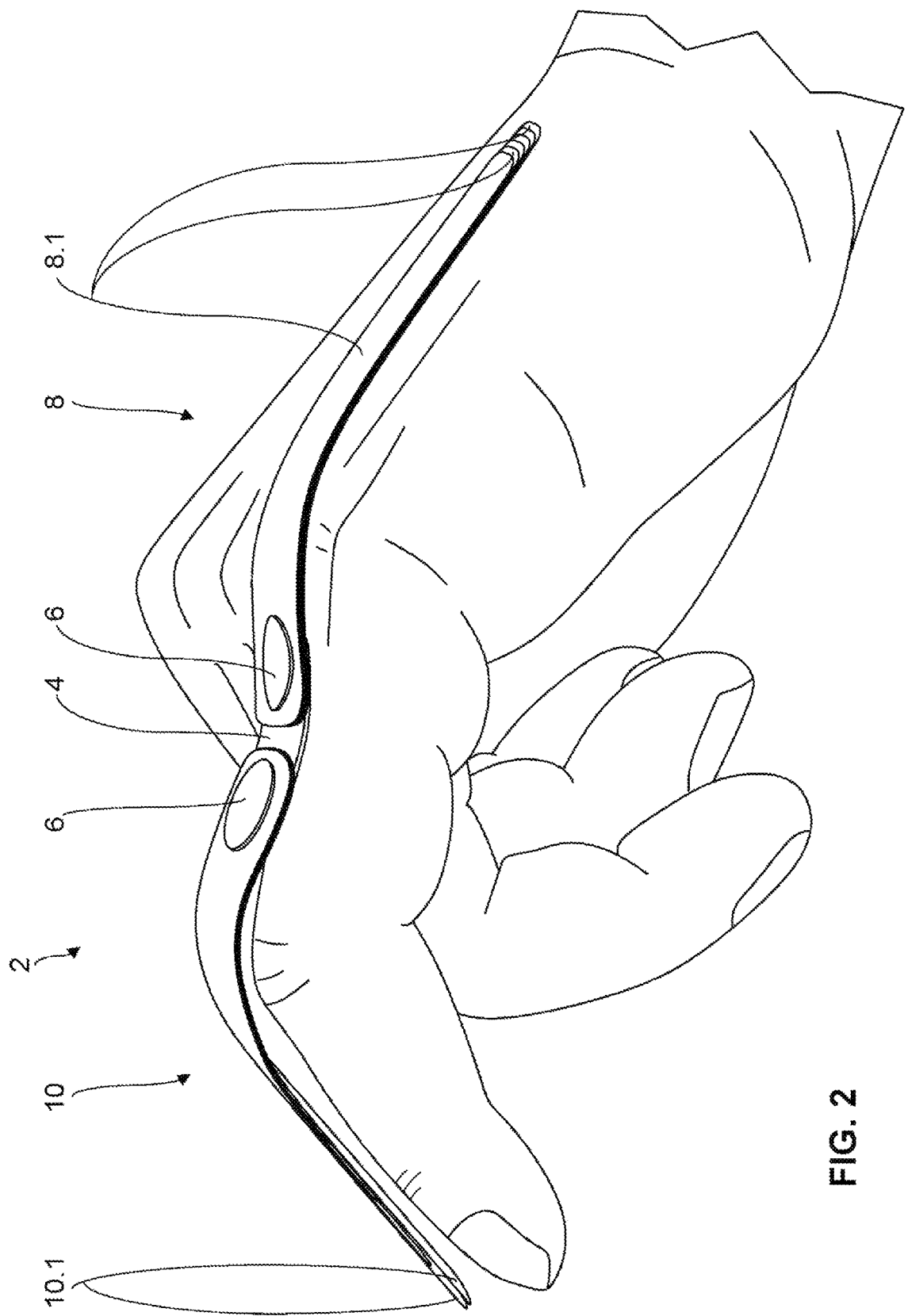

(58) Field of Classification Search
CPC .... A61F 2005/0179; A61F 5/10; A61F 3/023; A61F 3/027; A61F 1/18; A61F 5/0118; A61F 5/013; A41D 19/01582; A41D 19/01588; A41D 19/0024; A63B 21/4025; F16F 1/26
See application file for complete search history.

(56) References Cited

U.S. PATENT DOCUMENTS

| | | |
|---|---|---|
| 2006/0211964 A1 | 9/2006 | Farrell et al. |
| 2014/0142482 A1 | 5/2014 | Chung et al. |
| 2015/0366277 A1 | 12/2015 | Rabbeth, Jr. |

OTHER PUBLICATIONS

International Preliminary Report on Patentability for International Application No. PCT/DE2017/100533, dated Jan. 3, 2019.

* cited by examiner

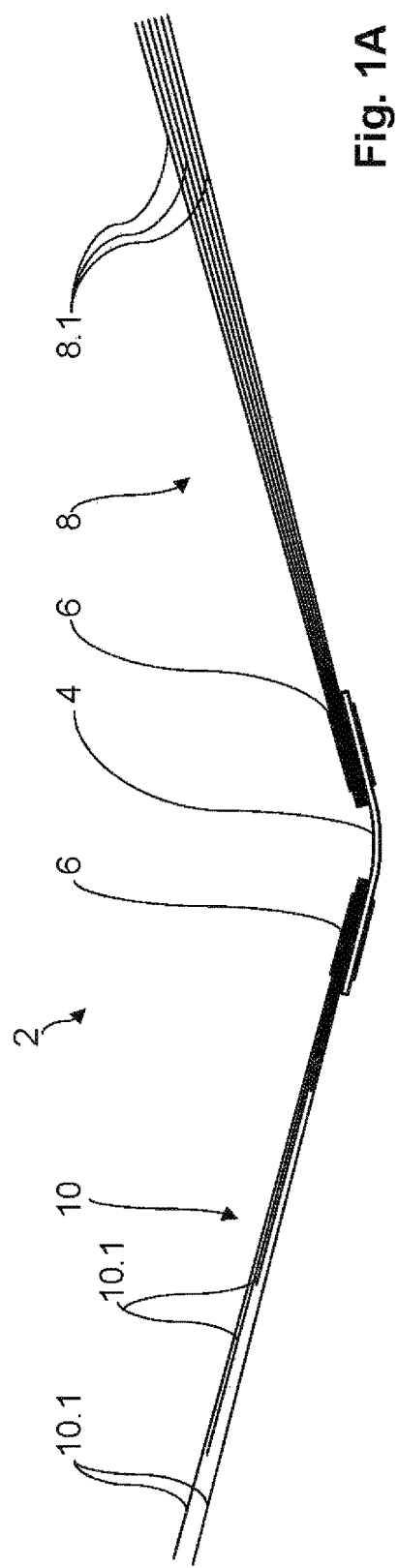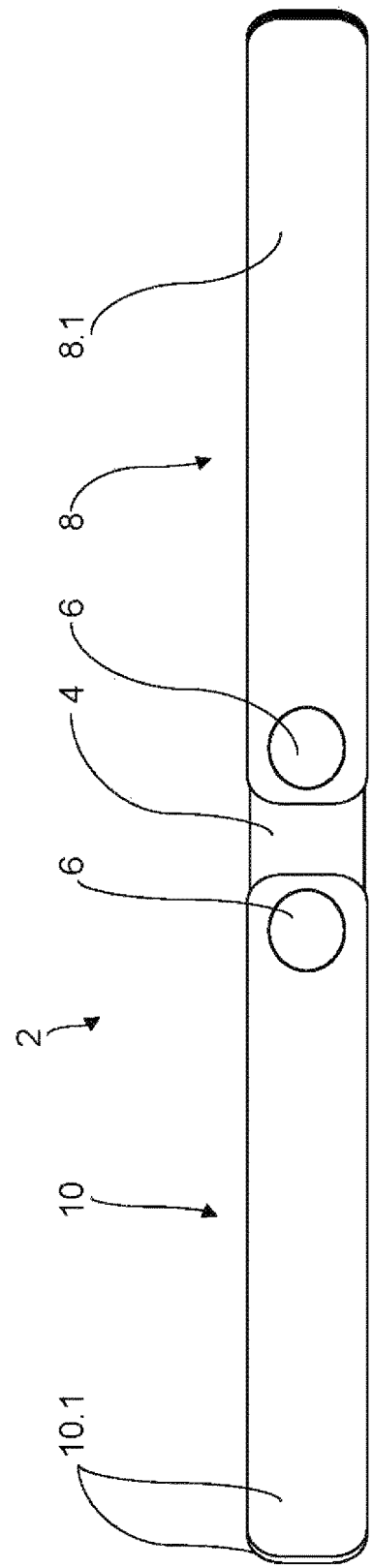
Fig. 1A
Fig. 1B

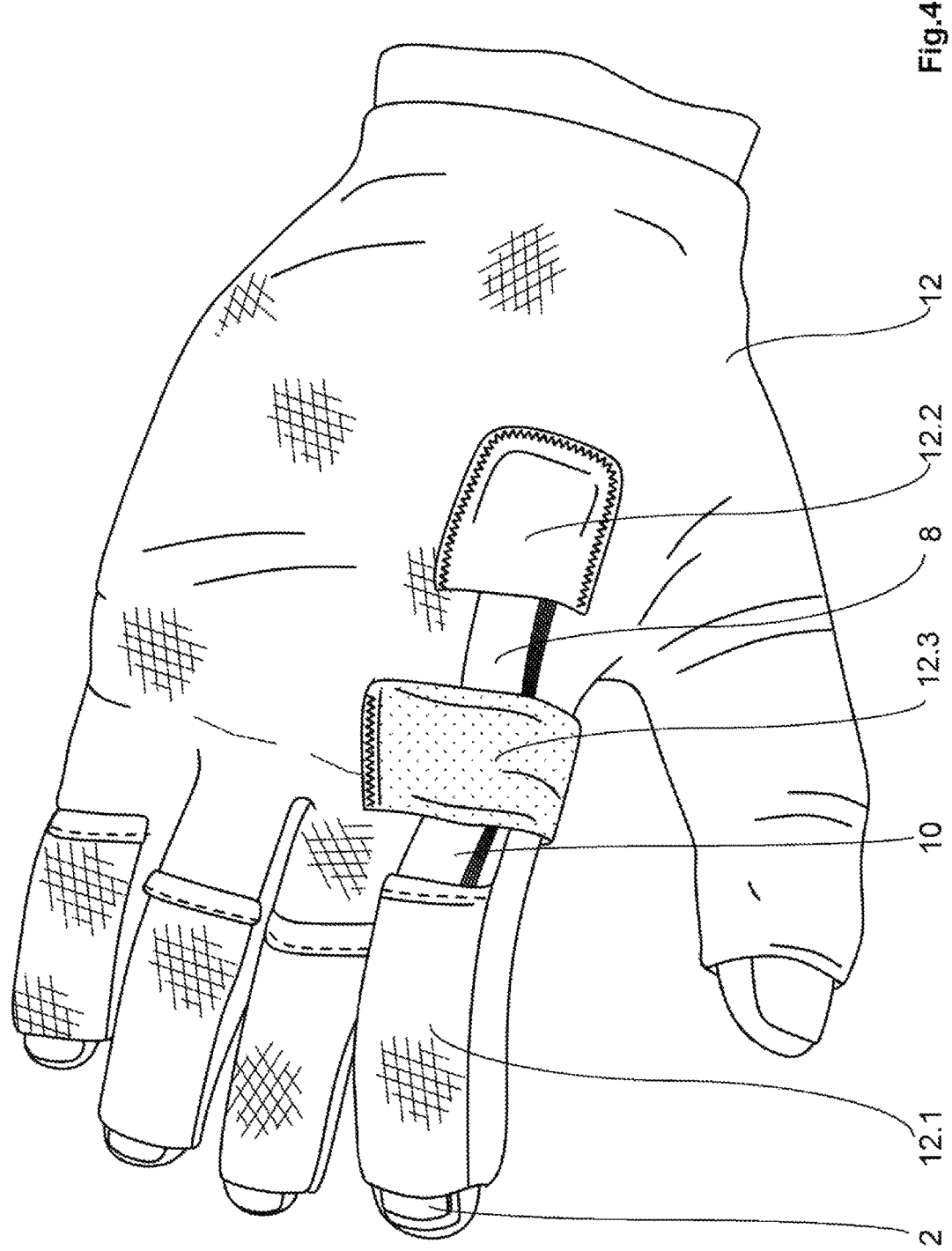

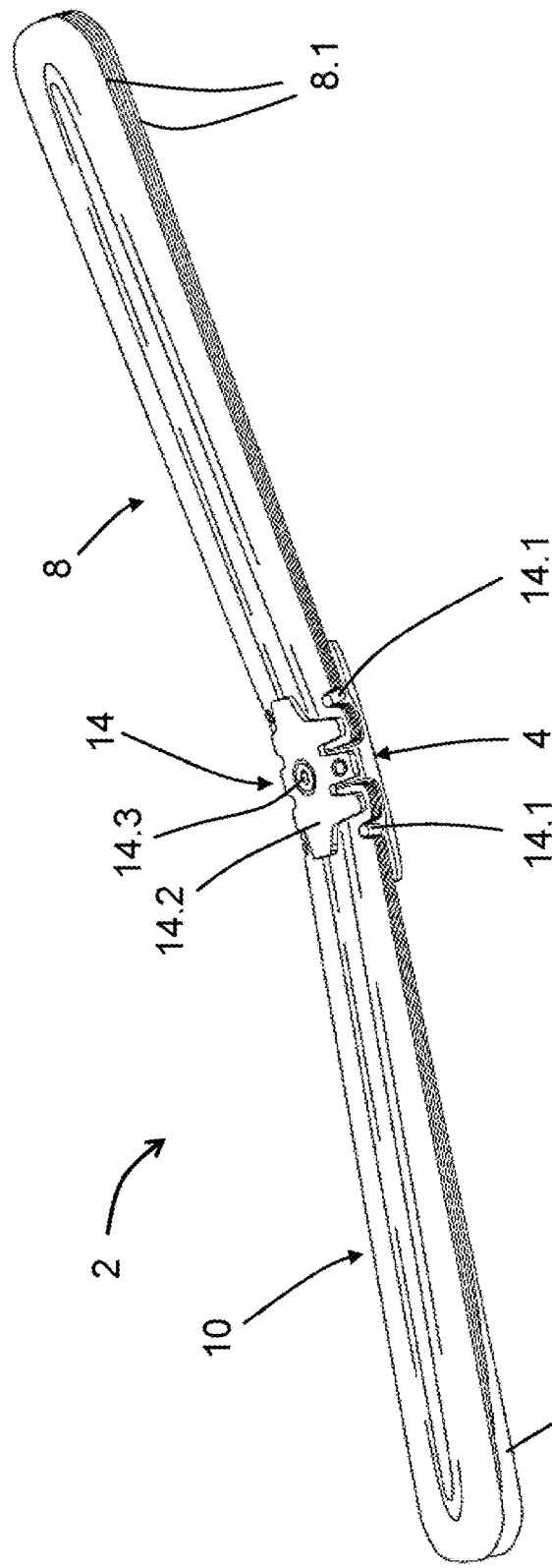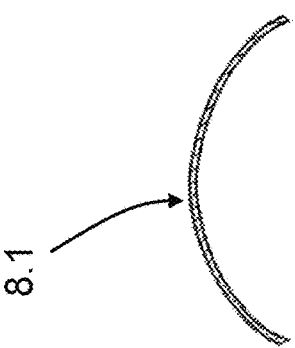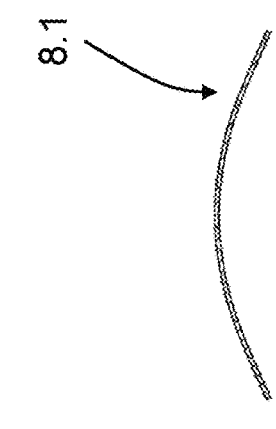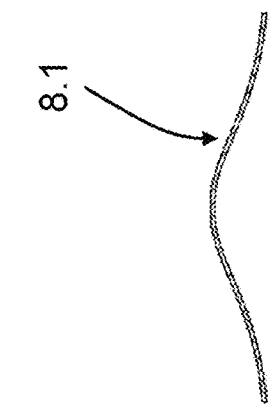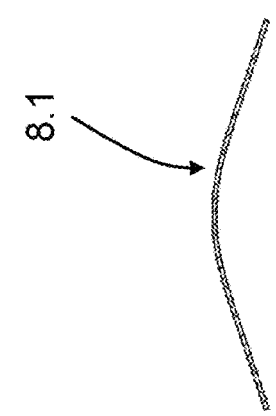

HAND ORTHOSIS

RELATED APPLICATIONS

This application is a national stage filing under 35 U.S.C. § 371 of international application number PCT/DE2017/100533, filed Jun. 23, 2017, which claims the benefit of European application number 17 166 900.5, filed Apr. 18, 2017, and claims the benefit of German application number 10 2016 116 014.8, filed Aug. 29, 2016, and claims the benefit of German application number 10 2016 111 644.0, filed Jun. 24, 2016, each of which is herein incorporated by reference in its entirety.

The invention relates to a hand orthosis with a glove and at least one finger splint, wherein the finger splint can be fixed to a hand by means of the glove.

Hand orthoses of this type are already known from the prior art in numerous embodiments, and serve to combat the progression of finger and thumb curvature or to prevent new curvature following surgical correction. The main application areas are so-called Dupuytren's contracture and finger curvature due to burn scars. In Dupuytren's contracture, connective tissue nodules and strands form in the palm and fingers between the skin and tendons; these are benign, but lead to increasing curvature of fingers and thumb, accompanied by increasing inability to use the affected hand.

All of the fingers and the thumb can be affected by Dupuytren's disease. The curvature that develops can involve an entire finger or thumb. In rare instances, isolated contracture of a finger or thumb joint may occur.

Hand orthoses of the type mentioned are used to push or pull the diseased fingers and/or thumb that can no longer be fully extended into an extended position over a certain time span. Thus the hand orthoses achieve passive extension and should be worn for several hours at a time if possible.

For example, a hand orthosis constructed as a therapy glove is known from DE 20 2011 104 828 U1. The glove serves for fastening an assembly designed as a fixing splint, consisting of a finger splint and baseplate, on a hand that is to be treated, with the known fixing splint made in one part. The fixing splint from DE 20 2011 104 828 U1 is made of sheet aluminum.

The goal of the present invention is to specify a hand orthosis in which the pull or push is distributed uniformly over the finger to be extended with the finger splint and at the same time, active countermovement of the finger is allowed.

To accomplish this goal, the invention is characterized according to the preamble of claim 1 in that the finger splint has at least one spring.

Here the term "finger" comprises both the regular fingers and the thumb. Correspondingly, in the following the term "finger" is generally used, for example in "finger splint," which is not to be understood as limiting. Insofar as is appropriate, use relating to the thumb is also meant.

The particular advantage of the invention is that a point tensile or compressive load on the extended finger or fingers is effectively avoided. This results in greater wearing comfort and thus higher acceptance of the hand orthosis according to the invention by the patients. As a result, the hand orthosis can be worn longer, for example. all night. When worn during the day it scarcely interferes with the intended use of the finger to be extended. In particular, active movement of the finger against the pulling or pushing force applied by the finger splint is possible. In this manner also stiffening of the finger is combated. Overall the treatment is more successful. Adverse effects, for example, pain, pressure ulcers or circulatory disturbances are largely avoided.

The hand orthosis according to the invention is especially suitable for straightening fingers affected by Dupuytren's contracture with a residual curvature of stage 1 according to Tubiana, thus of about 45° or less. For example, a residual curvature of this type is often present after surgery or needle fasciotomy. The causes of the residual curvature are primarily fibrosis strands still present or scar tissue surrounding the fibrosis strands, which is typically very firm. To stretch out this firm tissue, forces in the range of 2 N to 10 N are needed on the distal phalanx or 15 N to 50 N over the middle phalanx to the basal phalanx of the finger, applied for several hours daily at the beginning of treatment. Preferably the application of a tensile force is performed in that the finger splint is applied to the finger from the top and the tensile force is distributed over the largest possible area on the underside of the finger using a textile which surrounds the second and third finger joints as tautly as possible in the transverse direction but elastically in the longitudinal direction with air flow. The textile is thus part of the glove of the hand orthosis. If the finger orthosis according to the invention is used or applied regularly, it is sometimes possible to avoid a surgical operation altogether.

A particularly advantageous further development of the teaching according to the invention provides that the spring is provided in the form of a leaf spring, especially as a spring pack made of at least two stacked leaf springs. For example, the leaf springs of the spring pack may have the same length or different lengths. The leaf springs of different lengths in particular can be arranged in a cascade-like or stepped form. As a result, a desired distribution of the tensile or compressive force produced by the hand orthosis on the affected finger can be achieved with a simple design.

An advantageous further development of the above-mentioned embodiment provides that the spring pack is designed such that the tension or compression on the finger extended with the finger splint decreases from the proximal to the distal end of the finger. In this manner also, improved mobility of the affected finger or the finger to be treated is achieved.

Basically the finger splint can be selected within broad limits in terms of its type, arrangement, sizing, shape and material. Advantageously the finger splint, especially the spring, in a use position of the hand orthosis extends from the entire middle of the hand over the base joint, the base phalanx and the middle joint at least to the middle phalanx of the corresponding finger. It is especially advantageous if the finger splint, especially the spring, in a use position of the hand orthosis extends to the distal phalanx of the finger assigned to the hand orthosis. Thus essentially the entire length of the affected finger is included in the therapy. In this way the possible contact surface of the finger splint on the affected finger is maximized. Among other things, this leads to a lower tensile or compressive load on the individual finger areas.

In accordance with the additional further development of the invention, the at least one leaf spring is made of an elastically deformable, flexible steel. Particularly preferred is the use of spring steel or tape measure steel, as used, for example, in steel tape measures. For example, the steel has a thickness in the range of 0.1 mm to 0.3 mm, preferably a thickness of 0.15 mm to 0.25 mm and particularly preferably a thickness of 0.16 mm or 0.2 mm. A width of the steel corresponds, for example, approximately to an average width of the finger to be treated. If the splinted finger is moved, and especially curved, the position of the curvature in the case of the steel leaf spring or leaf springs glides very well. In this process the spring curves above the finger without contacting it. Thus during active curvature of the splinted finger, unwanted friction is avoided and the stress on the finger is reduced. This results in high wearing comfort.

According to a further development of the invention, the spring steel—as usual in the case of steel tape measures—is arched, in other words made in a curved shape. The arching or cambering is preferably accomplished perpendicular to the longitudinal extension (lengthwise) of the spring steel or the finger splint. Particularly preferably, the arching of the spring steel is formed in the same way over the total length, enabling easy manufacturing and resulting in a high inherent positional tolerance when applying the finger splint.

The arched leaf springs are applied with their upper side to the top of the finger. Preferably all springs in a spring pack are arched in the same way. The arching is produced, for example, by rolling, chamfering, bending or deep drawing.

Advantageously the arching makes it possible that in case of curvature of the finger over the joints, a bridge forms in the spring steel, which means that even in the case of curvature, resting of the spring steel on the finger joint and thus undesirable pressure loading in this area are avoided. Furthermore, essentially the same spring force arises over the various curvature angles of the finger, and essentially the spring force drops away suddenly or immediately when a straight position for the leaf spring and the finger fastened to it is achieved. Furthermore, due to the arching, as a result of the stiffening of the material, the spring force doubles based on the material used, thus the same amount of material used gives a greater spring force. Therefore the finger orthosis can be made very slim and lightweight.

Alternatively at least one leaf spring of the spring pack is made of a plastic and preferably of a fiber-reinforced plastic. Fiber-reinforced plastics in particular are light and strong. The mechanical properties of fiber-reinforced plastics can also be adjusted in the desired manner by means of a plurality of parameters. For example, the elasticity behavior may be made directional by alignment of the fibers. The spring pack consisting of at least two leaf springs can be produced and fastened in a suitable way known to the person skilled in the art.

It is advantageous if the finger splint is arranged on the outside of the hand and thus the assigned finger has a tensile force imposed on it. Also as a result, the finger to be treated as well as the affected hand as a whole undergoes less impairment of function.

A particularly simply designed realization of the embodiment according to the invention provides that the spring is bent doubly in the area of the basal joint of the assigned finger and is formed in such a manner that the spring has a stiffened or essentially rigid middle region, from which a first elastic distal region extends in the direction of the palm and a second elastic distal region extends in the direction of the middle phalanx of the assigned finger. If greater stiffness of the middle area of the spring is necessary, a stiffening plate can additionally be arranged in the middle area of the spring. When a plurality of stacked leaf springs are provided, these can be mechanically connected in the middle region. For example, a rivet connection can be provided to connect the leaf springs and simultaneously form the middle region.

An alternative embodiment provides that the finger splint has a finger plate arranged in the area of the metacarpophalangeal joint of the assigned finger, wherein at least one first and at least one second spring are arranged on the finger plate, from which the first spring extends in the direction of the metacarpus and the second spring extends in the direction of the middle phalanx of the assigned finger. Thus the first spring corresponds to the first elastic end region and the second spring to the second elastic end region of the previous embodiment. In this manner the adaptation of the individual spring regions to the requirements of the individual case is made especially easy. For example, the first and second springs may be made different from one another in terms of their type, material, number and shape. The geometry of the finger plate can be adapted to the geometry of the hand or the degree of finger curvature.

The finger plate can also be part of a middle module. The middle module is then applied with the finger plate in the area of the metacarpophalangeal joint of the assigned finger. At the same time, the middle module may be designed to accommodate a variable and modifiable number of springs, which extend in the direction of the metacarpus on one hand and the middle phalanx of the assigned finger on the other hand. For example, receiving pins for the springs may be provided on the middle module and the springs can be held in place by a pressure plate, retained movably with regard to the finger plate. For removable fastening, for example, a screw connection may be provided.

Advantageously the spring force can be adapted through the middle module by selecting a suitable number of springs and/or adapting the spring geometry to the course of treatment. For example, by reducing the springs over the treatment period, the spring force can be reduced, or the distribution of the spring force in the longitudinal direction of the fingers can be modified by changing the length, width and thickness of the individual springs.

If an isolated contracture is formed over the distal phalanx of the finger, the finger plate or the rigid middle area can be applied to the middle phalanx of the finger instead of the proximal phalanx, or it may be attached to the middle phalanx.

The additional subclaims and the description that follows present additional advantages, features and details of the invention. Each of the features mentioned there can be essential for the invention, individually or in arbitrary combinations. Thus mutual reference may be made to the disclosures on the individual invention aspects. The drawings relate to clarifying the invention and do not have a limiting character.

Figure 3:
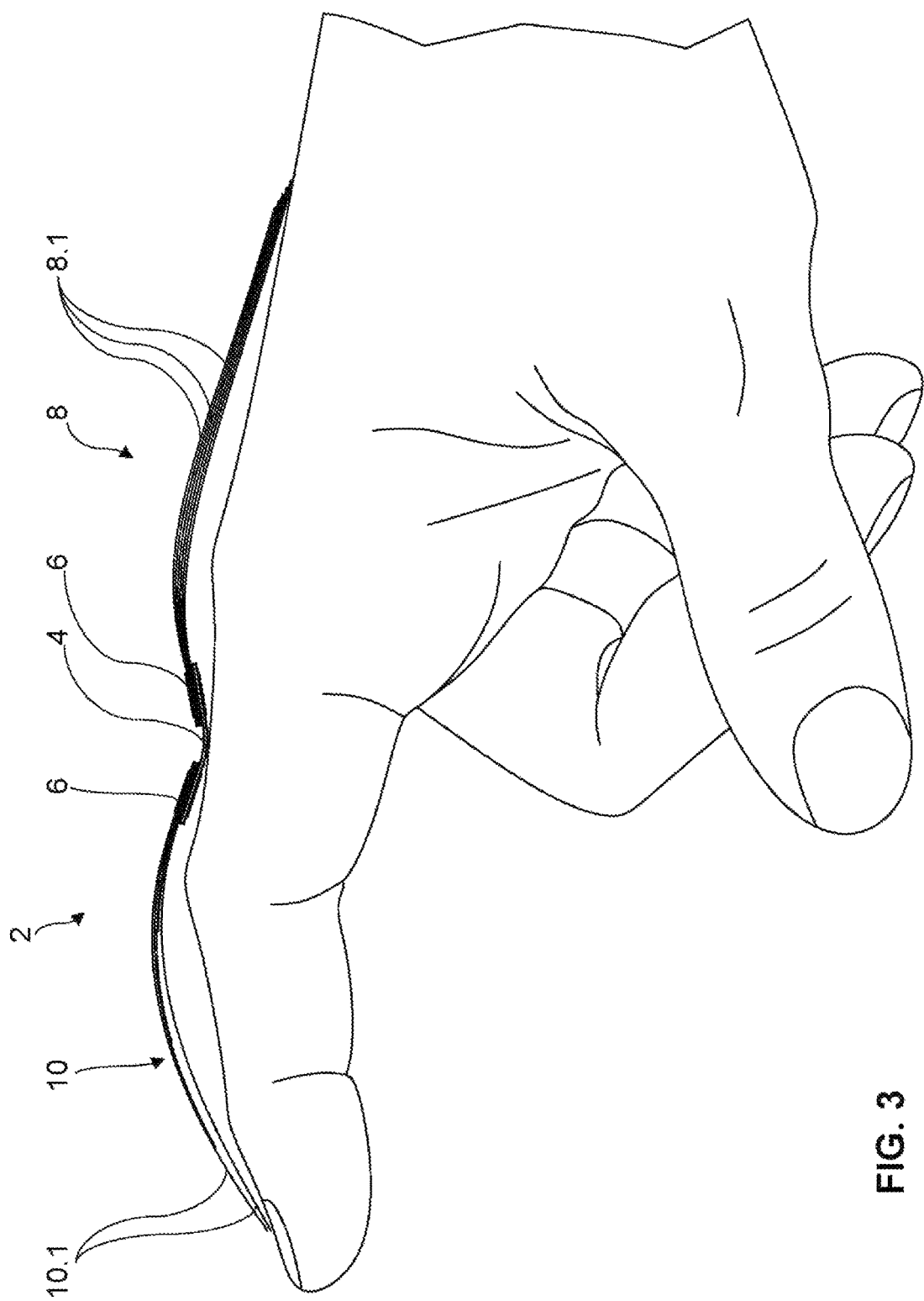
Figure 10:
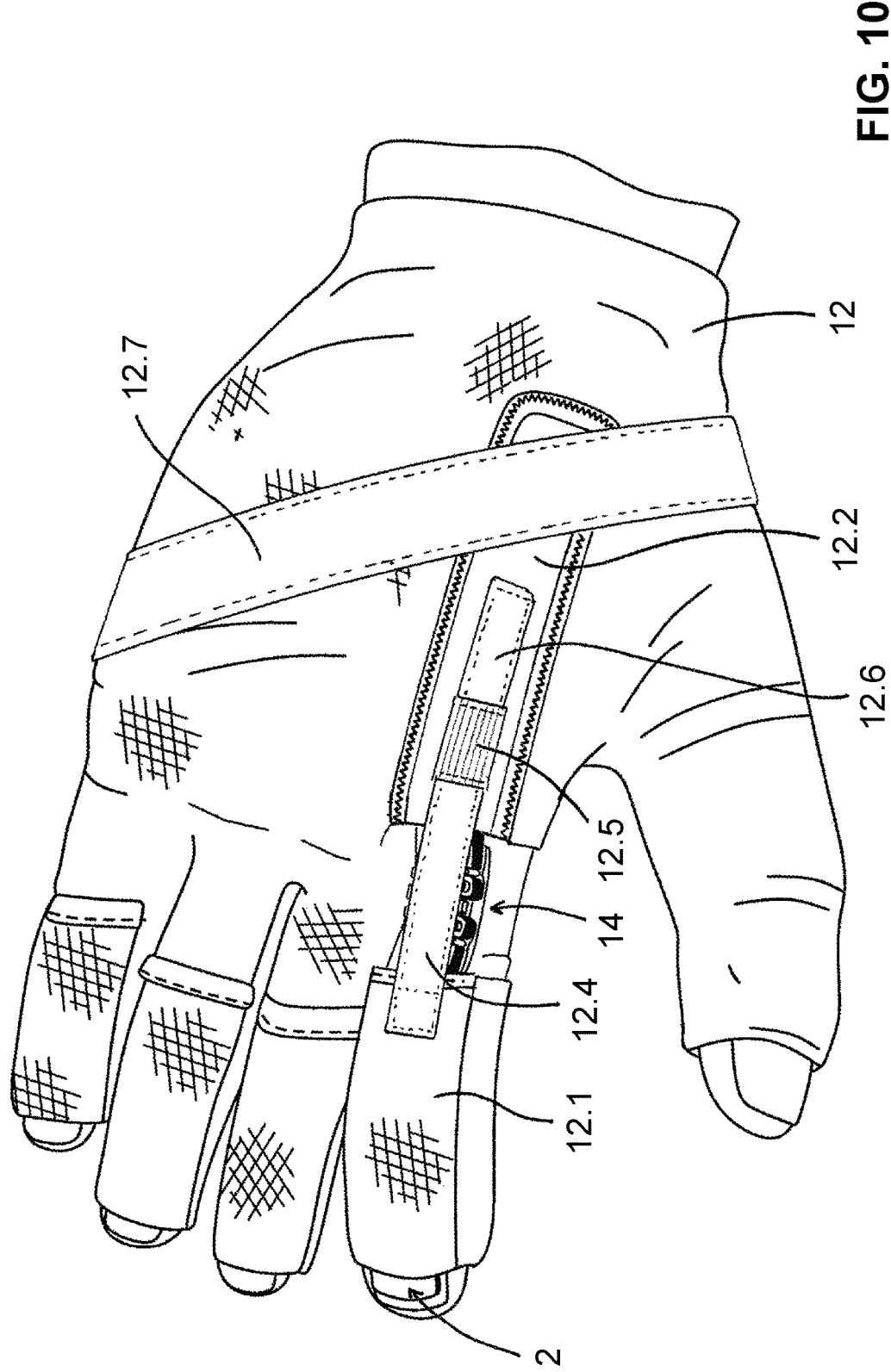

The following are shown:

FIG. 1A an exemplified embodiment of a finger splint of a hand orthosis according to the invention in partial view and in a side view;

FIG. 1B the exemplified embodiment of the finger splint from FIG. 1A in a partial top view;

FIG. 2 the exemplified embodiment of the finger splint from FIG. 1 in a first utilization position in a perspective, partial view;

FIG. 3 the exemplified embodiment of the same splint from FIG. 1 in a second utilization position in an additional perspective, partial view, FIG. 4 the exemplified embodiment from FIG. 1 in a third utilization position in a perspective view with the glove, FIG. 5 a perspective view of a second exemplified embodiment of the finger splint according to the invention with leaf springs of an arched shape, FIG. 6 a first cross-sectional geometry of a leaf spring of the finger splint according to FIG. 5, FIG. 7 an alternative, second cross-sectional geometry of a leaf spring of the finger splint according to FIG. 5, FIG. 8 an alternative third cross-sectional geometry of a leaf spring of the finger splint according to FIG. 5, FIG. 9 an alternative, fourth cross-sectional geometry of a leaf spring of the finger splint according to FIG. 5 and FIG. 10 the exemplified embodiment of the finger splint according to FIG. 5 of the invention in a perspective view with glove.

In FIG. 1A an exemplified embodiment of a hand orthosis according to the invention with a finger splint 2 is shown in a partial view. Here the finger splint 2 has a finger plate 4 made of aluminum, to which a first spring 8 and a second spring 10 are fastened over rivet connections 6. The first spring 8 and the second spring 10 are each made of spring packs 8, 10 from several layered leaf springs 8.1, 10.1 made of tape measure steel. Basically, however, the leaf springs 8.1, 10.1 can also be made of another flexible, elastically deformable steel, of plastic, and especially of fiber-reinforced plastic or the like.

The first spring pack 8 extends with its free ends, thus its elastic end regions, in the direction of the metacarpus and the second spring pack 10 extends with its free ends, thus its elastic end regions, in the direction of the middle phalanx or distal phalanx of the finger in question, thus the finger assigned to the hand orthosis. The metacarpus and the finger to be treated with the hand orthosis are shown only in FIGS. 2 and 3.

Here the first spring pack 8 has six leaf springs 8.1 of equal length, while the second spring pack 10 has three leaf springs 10.1 located on the inside and two leaf springs 10.1 located on the outside. The leaf springs 10.1 located on the inside are of different lengths relative to one another, beginning with the shortest leaf spring 10.1 on the side of the second spring pack 10 facing the finger plate 4. The two outer leaf springs 10.1 are of equal length and project beyond the leaf springs 10.1 on the inside. In this manner the leaf springs 10.1 on the inside are encompassed by leaf springs 10.1 located on the outside, which facilitates fixation in the glove, not shown in FIG. 1A, and thus on the affected hand and the finger to be treated.

The finger splint 2 with the finger plate 4 and the two spring packs 8, 10 is designed such that the assigned finger is subjected to tensile strength by the hand orthosis in its utilization position, wherein the tension on the finger extended with the finger splint 2 decreases from the proximal to the distal end of the finger. For this purpose also see the positions of the hand orthosis in use shown in FIGS. 2 and 3.

Thus the finger splint 2 is located on the exterior of the affected hand. In this way the function of the hand and fingers, not only of the finger to be treated, are less impaired than if the finger splint were arranged on the inside of the hand. This is especially true if several fingers are to be treated and thus several finger splints must be used simultaneously.

FIG. 1B shows the exemplified embodiment from FIG. 1A in a partial top view, thus—relative to the plane of the paper—with a viewing direction from the top in FIG. 1A.

FIG. 2 shows the hand orthosis from FIG. 1A and FIG. 1B in a first utilization position on an affected hand. The hand orthosis is shown in FIG. 2 without the glove to improve the visibility. The hand orthosis is applied on the affected finger, here the little finger and is fixed by the glove not only to the finger pad of the small finger and the metacarpus. Instead the finger splint 2 is in contact via the glove over a broad area with the finger being treated and thus is in force transfer connection with the affected finger. The advantage of this is that the tensile loading on the little finger is distributed essentially over the entire finger or the distal phalanx and the middle phalanx. At the same time, the load on the individual finger regions is correspondingly low. The little finger is shown in a curved position in the first utilization situation.

The finger splint 2 is arranged on a glove 12 shown only in FIG. 4 and is fixed to the hand to be treated and positioned by means of the glove 12. For example, the finger splint can be fastened to the glove by means of fastening pockets 12.1, 12.2 and strip 12.3. The finger splint 2 can even be an integral part of the glove 12. The glove 12 in the present exemplified embodiment, for better positioning of the finger splint 2 has a first fastening pocket 12.1 assigned to the finger to be treated and designed as an insertion pocket and a second fastening pocket 12.2 provided over the back of the hand. A fastening strap 12.3 provided in the area of the finger plate 4 is shown in this FIG. as a hook and loop fastener. Using the fastening strap 12.3 the hand orthosis can be attached in a particularly simple way, even by the patient.

As is clearly recognizable from FIG. 2, the finger splint 2 in a curved position of the finger with the finger plate 4 is adjacent to the proximal phalanx of the little finger. The positioning need not be done directly, but indirectly, for example if the finger splint 2 as shown in the existing embodiment according to FIG. 4 in this area is inserted into a fastening pocket or strap 12.1, 12.2, 12.3 of the glove 12. The first spring pack 8, starting from the finger plate 4, extends in the direction of the metacarpus. In this case the size of the attachment of the first spring pack 8 to the metacarpus determines the tensile force acting on the splinted finger. Then the second spring pack 10 in the usage position of the hand orthosis, starting from the finger plate 4, extends to the middle phalanx or distal phalanx of the little finger. As long as the finger is extended, the finger plate 4 must not contact the proximal phalanx. It is preferably kept at a distance from the finger by the spring 8 and somewhat floats over the proximal phalanx with the consequence that pressure is reduced and the comfort of wearing is promoted.

The little finger is placed under tensile stress by the hand orthosis. For this reason the two spring packs 8, 10 are supported against the finger plate 4 lying against the proximal phalanx. The finger plate 4 is correspondingly curved in the finger extension direction; also see FIG. 1A. Thus depending on the degree of curvature of the finger plate 4, the tensile force applied to the assigned finger can be adjusted or predetermined. The degree of bending of the finger plate 4 is an additional parameter for achieving the desired tensile load.

It is also apparent from FIG. 2 that the finger splint 2 of the hand orthosis in the first utilization position of the hand orthosis shown here extends from the metacarpus, over the metacarpophalangeal joint, the proximal phalanx, the middle joint, the middle phalanx and the distal joint to the pad of the little finger. It is also recognizable that the first spring pack 8 here is essentially positioned one-third in the area of the proximal phalanx of the little finger and two-thirds in the area of the metacarpus.

FIG. 3 shows the exemplified embodiment in a second utilization position. In contrast to FIG. 2, the index finger is shown here as the finger to be treated. The purpose of this is only to make clear the flexible application of the otherwise identical basic design. In FIG. 3 the finger to be treated shown in extended position; compare FIG. 2. Here also for the sake of visibility the hand orthosis is shown without the glove 12.

In FIG. 4 the complete hand orthosis of the present exemplified embodiment is illustrated in a utilization position analogous to FIG. 3. As was already stated regarding FIG. 3, it makes no difference for the explanation of the exemplified embodiment whether the finger to be treated is the little finger according to FIG. 2 or the index finger according to FIGS. 3 and 4. The basic structure of the hand orthosis according to the present exemplified embodiment is identical.

The fastening pocket 12.1 in the area of the middle phalanx and the distal phalanx of the finger being treated, into which the spring pack 10 is inserted is clearly recognizable, along with the fastening strap 12.3 in the area of the proximal phalanx of the index finger illustrated as a hook and loop closure, through which the finger plate 4, not shown in FIG. 4, can be easily fixed movably, and the fastening pocket 12.2, illustrated as an insertion pocket, into which the spring pack 8 is inserted with its free end.

An alternative embodiment of the finger splint 2 according to FIG. 5, as usual, a first spring pack 8 and a second spring pack 10, which as shown here are connected by a middle module 14 having the finger plate 4. The spring packs 8, 10 here are removably attached to the middle module 14. For this purpose the middle module 14 has a plurality of pins 14.1, which serve to fasten the leaf springs 8.1, 10.1 of the spring packs 8, 10. Thus corresponding to the pins 14.1 of the middle module 14, recesses 8.2, 10.2 are formed on the leaf springs 8.1, 10.1. In addition the middle module 14 provides a pressure plate 14.2, which is removably connected over a screw 14.3 with the finger plate 4. Between the finger plate 4 and pressure plate 14.2 here the leaf springs 8.1, 10.1 of the spring packs 8, 10 are fastened.

The provision of the middle module 14 with the removably attached pressure plate 14.2 makes it possible to select the number of leaf springs 8.1, 10.1 and the geometry thereof to be variable and, especially, to adjust them to the progress of treatment as the treatment continues. At the same time the finger plate 4, which is attached in the area of the proximal phalanx to the finger from the top guarantees that the comfort of wearing is maintained or at least not affected negatively.

For example, it is shown in FIG. 5 that the leaf springs 8.1, 10.1 are arched. The arched shape is realized such that finger splint 2 is attached with its hollow side from above on the splinted finger and on the back of the hand. As a result of the arched shape the finger can be bent, wherein even with a curvature over a joint of the finger, the spring pack 8, 10 forms a bridge and is provided at a distance from the joint. Preferably the bridge is always formed exactly in the center above the joint. In particular the bridge formation avoids mechanical contact and prevents uncomfortable pressure loading. As a result, the wearing comfort of the finger splint according to the invention is increased.

Alternative embodiments of the arching are shown as examples in FIGS. 6-9. FIGS. 6-9 show an individual leaf spring 8.1 as an example in cross-section, i.e., transfers to the lengthwise extension of the leaf spring 8.1. It is preferably provided that all leaf springs 8.1, 10.1 of the spring packs 8, 10 are arched in the same way and thus can be placed directly one on top of the other in a laminar pattern.

The finger splint 2 according to FIG. 5 is inserted in a glove 12 in FIG. 10. For this purpose the first spring pack 8 and the second spring pack 10 are inserted into the fastening pockets 12.1, 12.2 of the glove 12. The positioning of the finger splint 2 on the hand is accomplished in that the middle module the center module 14 is provided with the finger plate 4 over the proximal phalanx of the splinted finger. The spring packs 8, 10 with the springs 8.1, 10.1 having an arched design are placed on the fingers and the back of the hand with the hollow side at the top.

The fixation of the finger splint 2 to the glove 12 and/or the hand in the present case is accomplished first by way of a retaining strap 12.4, which is guided from the first fastening pocket 12.1 receiving the second packet 10 in the direction of the second fastening pocket 12.2, a flexible strap 12.5 following the retaining strap 12.4, and a hook and loop strap 12.6, which is connected to the flexible strap 12.5 and is fastened movably to the second fastening pocket 12.2. The surface of the fastening pocket 12.2 and the hook and loop strap 12.6 thus form the two sides of a hook and loop connection.

Furthermore the fastening is achieved with a lashing strap 12.7, which in the position of use is guided over the back of the hand and presses the first spring pack 8 against the back of the hand. Preferably a spring element is inserted in the lashing strap 12.7, which exerts a variable force on the first spring pack 8, simultaneously increasing the comfort of wearing and promoting secure attachment.

The invention is not limited to the exemplified embodiment explained on the basis of FIGS. 1-10.

Although the present exemplified embodiment relates to the use of the hand orthosis according to the invention on a human hand, use on an animal's paw would also be conceivable.

In individual cases it may be advantageous to place at least one finger splint of the hand orthosis according to the invention on the inside of the hand in the position of use. Correspondingly, pressure would be applied to the damaged finger or fingers by a hand orthosis of this type. It is also possible for finger splints to be placed on both the inside and the outside of the hand.

Then, finger splints of this type can be applied to different fingers or to a single finger to be treated.

The person skilled in the art, depending on the specific application, will select the required number of leaf springs and the length thereof for each individual finger to be treated. Correspondingly the number of leaf springs need not necessarily be identical for each spring pack or each finger splint.

Positioning of the spring packs 8, 10 at a shallow angle relative to one another can be achieved as in the exemplified embodiment according to FIG. 1A in that the finger plate 4 is designed with a curve. For example, the position can be achieved using wedge inserts provided between the spring packs 8, 10 and the finger plate 4. The wedge inserts can thus also be used in the case of the center module 14.

By means of the glove to which the at least one finger splint of the hand orthosis is fastened or in which it is integrated, both could transfer a force from the hand orthosis to the diseased finger on the hand and good comfort in wearing can be achieved. Correspondingly the design of the hand orthosis according to the invention is very simple and thus cost-advantageous. Through the suitable attachment of fastening straps and pockets the at least one finger splint can be positioned reliably relative to the assigned finger, thus the finger to be treated.

In the exemplified embodiment explained, the glove is designed as a full glove except for the finger tips. Basically, however, it is possible for only the one or more fingers to be treated or gloved, or that the fingers that are not affected are only partially surrounded by the glove. This can be the case over the entire finger length and over only a partial length of the finger.

It is also possible to design the glove as a universal glove which provides fastening elements, for example, fastening straps and pockets or the like, for receiving a finger splint or several finger splints for a plurality of fingers. The glove of the exemplified embodiment has the fastening elements for the finger splint on the outside of the hand. In other applications, however, the fastening elements could also be positioned on the hand inside of the glove or the hand inside and the hand outside of the glove.

With the hand orthosis of the invention, the tensile or pressure application applied on the finger to be treated is distributed more uniformly thereon. In addition more reliable positioning of the finger splint is facilitated.

Instead of the rivet connections 6 fixed between the finger plate 4 and the first and second spring packs 8, 10, other connecting technologies known to the person skilled in the art and suitable for this purpose are possible.

The finger splint of the hand orthosis need not necessarily extend to the finger pad of the affected finger. However, extension to the distal phalanx of the assigned finger is advantageous, since in this way the load on the finger is distributed even better by the hand orthosis and a better lever effect is achieved.

The arched design of the leaf springs 8.1, 10.1 is shown as an example for the exemplified embodiment according to FIG. 5. According to the invention the arched design of the leaf springs 8.1, 10.1 can also be used for the finger splints according to FIGS. 1-4 and any other finger splints. The arching is thus also not limited to the use of the center module 14. In particular the arching can be used in the design of the finger plate 4 and/or together with a rivet connection 6 for the spring packs 8, 10.

The at least one spring of the finger splint need not have the design according to the exemplified embodiment. For example, it is conceivable that only a single spring or a single spring pack consisting of multiple layered leaf spring is used. Thus the finger splints could also consist of a single spring or a single spring pack. In analogy to the finger splint of the exemplified embodiment, this spring or this spring pack, in a utilization position of the hand orthosis, can extend from the metacarpus, over the metacarpophalangeal joint, the proximal phalanx and the middle joint at least to the middle phalanx, preferably to the distal phalanx, of the assigned finger.

In an initial phase of the therapy, for example, six to 25 springs are combined to form a pack to supply the necessary force. In a later phase of therapy then the spring force, for example, of a single spring may be adequate to achieve residual full straightening of the finger being treated or, for example, to maintain straightening achieved following surgery.

Alternatively to the exemplified embodiment explained based on FIGS. 1-10, the single spring or the single spring pack can be designed to be doubly bent in the area of the proximal phalanx of the assigned finger in such a manner that the spring or the spring pack has an essentially rigid middle region, from which a first elastic terminal region extends in the direction of the metacarpus and the second elastic terminal region extends in the direction of the middle phalanx of the assigned finger.

Thus in the case of one spring pack, the individual leaf springs of the spring pack in the first case would simply be placed on inside of the other. Due to the special design of each leaf spring with the two bending sites and the middle region formed in this way, the individual leaf springs slid into the treatment glove as a spring pack would automatically maintain their position in the spring pack even when the hand orthosis was in use. However it would also be conceivable that the individual leaf springs of the spring pack would be fixed together by fastening means such as rivets or the like. For example, a rivet connection could be provided at each end of the middle region formed by the bending points.

This middle region would then take over the function of the finger plate 4 of the exemplified embodiment. To increase the stiffness of the middle region formed in this way it would be conceivable to supply a stiffening plate in the middle region of the splint. This stiffening plate, for example, in analogy to the exemplified embodiment could be fastened with two rivet connections to the spring or the spring pack.

Another alternative embodiment provides that the finger splint is fastened through a baseplate, wherein the baseplate is fixable by the glove in the area of the metacarpus and the finger splints, especially the springs, in the use position of the hand orthosis extends from the base plate, over the proximal joint, the proximal phalanx and the middle joint at least to the middle phalanx, especially to the distal phalanx, of the assigned finger. Thus in this embodiment only one free end of the spring or the spring pack and thus only one elastic end would be formed.

In contrast to known hand orthoses, the hand orthosis according to the invention can be better adapted for use in a later stage of therapy, thus when the fingers are extended fairly far. The hand orthosis according to the invention has a lower weight, causes less limitation of the freedom of motion of the affected hand and the affected finger, and thus offers higher comfort in wearing.

In addition to the materials mentioned for the finger plate and the leaf springs, other materials known to the expert and suitable for use are conceivable. A combination of materials differing from one another for the finger plate, the leaf springs, the spring packs and other components of the hand orthosis according to the invention are possible.

Optionally according to the invention it can be provided that a silicone cushion is present on the finger splint 2 on a side facing the finger and/or the back of the hand in its utilization position, at least in one section. The silicone cushion can provide a soft contact surface and contribute to improve the wearing comfort.

LIST OF SYMBOLS

2 Finger splint
4 Finger plate
6 Rivet connector
8 First spring, formed as the first spring pack made of multiple leaf springs
8.1 Leaf springs of the first spring pack
8.2 Recess
10 Second spring, formed as the second spring pack made of multiple leaf springs
10.1 Leaf springs of the second spring pack
10.2 Recess
12 Glove
12.1 Fastening pocket, formed as insertion pocket
12.2 Fastening pocket, formed as insertion pocket
12.3 Fastening strip, formed as a hook-and-loop strap
12.4 Retaining strap
12.5 Hook-and-loop strap
12.7 Lashing strap with inserted spring element
14 Middle module
14.1 Pin
14.2 Pressure plate
14.3 Screw

The invention claimed is:

1. A hand orthosis configured to treat Dupuytren's contracture comprising a glove and at least one finger splint, wherein the at least one finger splint is configured to be fixed to a hand and positioned by means of the glove, characterized in that the at least one finger splint comprises at least one spring;

wherein the at least one finger splint is configured to extend in a utilization position of the hand orthosis from a metacarpus, over a metacarpophalangeal joint, a proximal phalanx and a middle joint at least to a middle phalanx of an assigned finger;

wherein the at least one spring is configured to be doubly bent in an area of the proximal phalanx between the metacarpophalangeal joint and the middle joint of the assigned finger so that the at least one spring has a rigid middle region, from which a first elastic distal area is configured to extend in a direction of the metacarpus and a second elastic distal area is configured to extend in a direction of the middle joint of the assigned finger;

wherein the at least one spring is configured to have an arched shape, with a curvature transverse to a longitudinal direction of the at least one finger splint and is configured to place the assigned finger under tensile stress in a bending position with the rigid middle region configured to lay against and be supported by the proximal phalanx by means of the glove and wherein the first elastic distal area is configured to form a first bridge over and be spaced apart from at least the middle joint and wherein the second elastic distal area is configured to form a second bridge over and be spaced apart from at least the metacarpophalangeal joint.

2. The hand orthosis according to claim 1, characterized in that the at least one spring is formed as a spring packet of at least two layered leaf springs.

3. The hand orthosis according to claim 2, characterized in that the spring packet is designed such that the tension or pressure on a finger extended with the at least one finger splint decreases from a proximal to a distal end of the finger.

4. The hand orthosis according to claim 2, wherein the at least two layered leaf springs are made of a flexible, elastically deformable steel.

5. The hand orthosis according to claim 4 wherein the at least two layered leaf springs are made of a spring steel and/or tape measure steel.

6. The hand orthosis according to claim 1 characterized in that the at least one finger splint is configured to extend in a utilization position of the hand orthosis from the metacarpus, over the metacarpophalangeal joint, the proximal phalanx and the middle to a distal phalanx, of the assigned finger.

7. The hand orthosis according to claim 1, characterized in that a stiffening plate is located on the rigid middle region of the at least one spring.

8. The hand orthosis according to claim 1, characterized in that the at least one finger splint in the utilization position of the hand orthosis is configured to be positioned on the assigned finger with a hollow side of the springs from a top.

9. The hand orthosis according to claim 1, characterized in that the at least one finger splint is fastened to a base plate, wherein the base plate is configured to be fixable in an area of the middle of the hand by means of the glove, and the at least one finger splint in the utilization position of the hand orthosis is configured to extend from the base plate, over the metacarpophalangeal joint, at least to the middle joint of the assigned finger.

10. A hand orthosis configured to treat Dupuytren's contracture comprising a glove and at least one finger splint, wherein the at least one finger splint is configured to be fixed to a hand and positioned by means of the glove, characterized in that the at least one finger splint comprises at least one spring, wherein the at least one finger splint is configured to extend in a utilization position of the hand orthosis from a metacarpus, over a metacarpophalangeal joint, a proximal phalanx, and a middle joint at least to a middle phalanx of an assigned finger;

characterized in that the at least one finger splint is configured to have a finger plate positioned in the area of the proximal phalanx of the assigned finger by means of the glove, wherein at least one first and at least one second spring are arranged on the finger plate, and wherein the at least one first spring is configured to extend in a direction of the metacarpus and the at least one second spring is configured to extend in a direction of the middle phalanx of the assigned finger;

wherein the springs are configured to have an arched shape, with a curvature transverse to a longitudinal direction of the at least one finger splint and to place the assigned finger under tensile stress in a bending position with the finger plate configured to lay against and be supported by the proximal phalanx, and wherein the at least one first spring is configured to form a first bridge over and be spaced apart from at least the middle joint and the at least one second spring is configured to form a first bridge over and be spaced apart from at least the metacarpophalangeal joint.

11. The hand orthosis according to claim 10, characterized in that the at least one first spring is formed as a spring pack with springs of equal length and/or the at least one second spring is formed as a spring pack with at least one inner spring and two outer springs projecting lengthwise beyond the inner spring in length.

12. The hand orthosis according to claim 10, characterized in that the at least one first spring is configured to be one-third in the area of the proximal phalanx of the assigned finger and two-thirds in the area of the middle phalanx.

13. The hand orthosis according to claim 10, characterized in that the finger plate is designed as part of a middle module and that the springs are fastened to the middle module between the finger plate and a pressure plate of the middle, wherein the finger plate and the pressure plate are connected removably with one another.

14. The hand orthosis according to claim 10, characterized in that the at least one finger splint is fastened to a base plate, wherein the base plate is configured to be fixable in an area of the middle of the hand by means of the glove, and the at least one finger splint in the utilization position of the hand orthosis extend from the base plate, over the metacarpophalangeal joint, at least to the middle joint of the assigned finger.

* * * * *